United States Patent
Liu et al.

(10) Patent No.: US 9,689,743 B2
(45) Date of Patent: Jun. 27, 2017

(54) ACCURACY AND PRECISION IN RAMAN SPECTROSCOPY

(75) Inventors: Huiwen Liu, Eden Prairie, MN (US); Peter Gunderson, Ellsworth, WI (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 416 days.

(21) Appl. No.: 13/559,211

(22) Filed: Jul. 26, 2012

(65) Prior Publication Data

US 2014/0028996 A1    Jan. 30, 2014

(51) Int. Cl.
    *G01J 3/44*       (2006.01)
    *G01J 3/00*       (2006.01)
    *G01J 3/02*       (2006.01)
    *G01N 21/65*     (2006.01)

(52) U.S. Cl.
    CPC ........... *G01J 3/0248* (2013.01); *G01J 3/0237* (2013.01); *G01J 3/0278* (2013.01); *G01J 3/44* (2013.01); *G01N 21/65* (2013.01)

(58) Field of Classification Search
    CPC .... G01N 21/65; G01N 21/658; G01N 21/255; G01N 2201/1087; G01J 3/44; G01J 3/0208; G01J 3/0237
    USPC .................................................. 356/301, 51
    See application file for complete search history.

(56) References Cited

U.S. PATENT DOCUMENTS

| | | |
|---|---|---|
| 6,008,894 A | 12/1999 | Schmucker |
| 6,961,080 B2 | 11/2005 | Richardson |
| 7,116,416 B1 * | 10/2006 | Boss et al. ..................... 356/301 |
| 7,336,351 B1 | 2/2008 | Sweatt |
| 7,474,397 B2 | 1/2009 | Wang |
| 7,586,603 B2 | 9/2009 | Maity |
| 7,955,768 B2 | 6/2011 | Tada |
| 8,054,461 B2 | 11/2011 | Kuo |
| 2006/0038980 A1 * | 2/2006 | Naka et al. ..................... 356/73 |
| 2006/0088139 A1 * | 4/2006 | Nakano et al. .................. 378/79 |
| 2007/0049831 A1 * | 3/2007 | Crowther .................. G01J 3/44 600/473 |
| 2008/0137081 A1 * | 6/2008 | Murakami ........... G01N 21/658 356/301 |
| 2009/0002700 A1 * | 1/2009 | Wang et al. ................... 356/301 |
| 2009/0213369 A1 * | 8/2009 | Lee et al. ....................... 356/301 |

(Continued)

*Primary Examiner* — Tarifur Chowdhury
*Assistant Examiner* — Sunghee Y Gray
(74) *Attorney, Agent, or Firm* — Cesari & Reed, LLP; Kirk A. Cesari; Christian W. Best

(57) ABSTRACT

The disclosure is related systems and method for improved accuracy and precision in Raman spectroscopy. In one embodiment, a device may comprise a Raman spectroscopic apparatus configured to determine a property of a sample by directing photons at the sample and measuring a resulting Raman scattering, a positioning apparatus capable of manipulating a position of the sample, and the device being configured to selectively adjust a focus of the Raman spectroscopic apparatus to adjust an intensity of the Raman scattering. Another embodiment may be a method comprising performing a depth focus Raman spectra screening on a sample to determine a depth focus with a maximum-intensity Raman spectra, wherein the depth focus spectra screening comprises performing Raman spectra scans on the sample at a plurality of depth foci, and modifying a process based on a result of the Raman spectra scan at the depth focus with the maximum-intensity Raman spectra.

19 Claims, 3 Drawing Sheets

(56) References Cited

U.S. PATENT DOCUMENTS

2010/0277723 A1* 11/2010 Rezac et al. .................. 356/301
2012/0162660 A1*  6/2012 Kemp .......................... 356/479
2012/0314206 A1* 12/2012 Spizig et al. ................... 356/72

* cited by examiner

| Raman Testing Condition | | 1 Gage Sigma |
|---|---|---|
| With accurate Z-focus adjustment | No Filter | 1.7 A |
| | Filter | 0.9 A |
| With no Z-focus adjustment | No Filter | 3.1 A |
| | Filter | 2.4 A | ium
ACCURACY AND PRECISION IN RAMAN SPECTROSCOPY

BACKGROUND

The field of Spectroscopy is related to the study of the interaction between matter and radiated energy. Generally, spectroscopy refers to the process of measuring energy or intensity as a function of wavelength in a beam of light or radiation. Raman spectroscopy is a spectroscopic technique which can be used to measure the molecular structure of a tested sample. Raman spectroscopy relies on the inelastic scattering of intense, monochromatic light, typically from a laser source operating in the visible, near infrared, or ultraviolet range. For example, a laser may be directed at a sample, and the Raman scattered light can be measured to determine various properties of the sample.

In particle physics, elastic scattering is a form of scattering where the kinetic energy of the incident particles is conserved, and only their direction of propagation is modified by interaction with other particles. Inelastic scattering, as involved in Raman spectroscopy, has the incident photon gaining or losing kinetic energy on interaction with other particles. Inelastic Raman-scattered particles may be less common or less intense than elastic scattered particles (sometimes called Rayleigh scattering), and can be challenging to measure. Therefore, systems and methods are needed for improved accuracy and precision in Raman spectroscopic techniques.

SUMMARY

A device may comprise a Raman spectroscopic apparatus configured to determine a property of a sample by directing photons at the sample and measuring a resulting Raman scattering, a positioning apparatus capable of manipulating a position of the sample in relation to the Raman spectroscopic apparatus, and the device being configured to selectively adjust a focus of the Raman spectroscopic apparatus in relation to the sample to adjust an intensity of the Raman scattering.

In another embodiment, a method may comprise adjusting a position of a sample on a plane substantially perpendicular to an angle of a light beam emitted from a Raman spectroscopic laser, performing a Raman spectra focus screening on the sample to determine a focus depth setting of the Raman spectroscopic laser in relation to the sample based on a Raman spectra scattering intensity from the Raman spectra focus screening, and performing a Raman spectra test on the sample at the focus depth setting.

Another embodiment may be a method comprising performing a depth focus Raman spectra screening on a test sample to determine a depth focus with a maximum-intensity Raman spectra, wherein the depth focus spectra screening comprises performing Raman spectra scans on the test sample at a plurality of depth foci, and modifying a process based on a result of the Raman spectra scan at the depth focus with the maximum-intensity Raman spectra.

DETAILED DESCRIPTION

In the following detailed description of the embodiments, reference is made to the accompanying drawings which form a part hereof, and in which are shown specific embodiments by way of illustration and not limitation. It is to be understood that other embodiments may be utilized and structural changes may be made without departing from the scope of the present disclosure.

Raman spectroscopy has a variety of applications, and Raman testing can be performed on various types of matter. For example, Raman testing can be performed on samples produced in a manufacturing process to monitor the qualities of the samples, and adjust the manufacturing process to produce products with the desired qualities. In an example embodiment, Raman testing may be used to measure the thickness of diamond-like carbon protective coatings on magnetic recording heads for hard disc drive storage devices. Control of the coating thickness can be very important for reliability, head-media spacing, and other aspects of head sliders. Similar testing on micro-size samples can be dramatically improved through the use of the systems and methods disclosed herein.

Figures 1, 2:
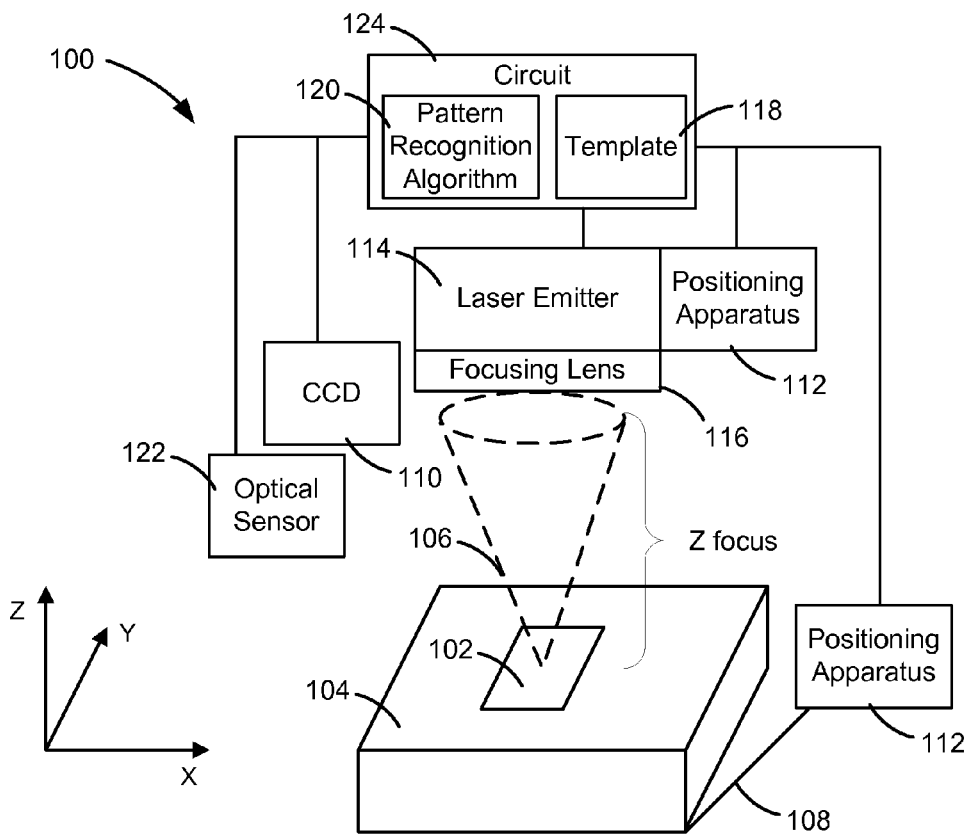
FIG. 1 is a diagram of an illustrative embodiment of a system for improved accuracy and precision in Raman spectroscopy.
FIG. 2 is a table of results from an illustrative embodiment of a system for improved accuracy and precision in Raman spectroscopy.

FIG. 1 depicts an example embodiment of a system for improved accuracy and precision in Raman spectroscopy, generally designated 100. The system 100 may be a spectroscopic apparatus (i.e. capable of performing spectroscopy) used to test samples. In system 100, a sample 102 may be placed upon a platform 104 to undergo Raman testing. Intense, monochromatic light in the form of photons, such as a laser 106, can be focused on the sample 102, and the Raman scattered light can be measured. Raman scattered light may be measured by using instruments such as Charge-Coupled Devices (CCDs) 110, although other measuring methods or instruments may also be used.

The sample 102 to be tested may be extremely small, for example in the scale of micrometers (ums). Testing may be performed on multiple locations of the sample 102 by adjusting the laser 106 relative to the sample 102. The sample 102 or the laser 106 may be positioned and adjusted using positioning apparatus 112 either manually or by automated means. For example, in some embodiments the platform 104 may be part of a high-precision piezo scanner capable of making extremely minute position changes (e.g. in nanometer scale) in response to an applied voltage. The piezo scanner may be operated by software, firmware, hardware, an operator, or a combination thereof, and may adjust the positioning of the platform 104 and the sample 102 thereon to position and adjust the sample for scanning. The platform 104 may be mounted to a movable or adjustable arm 108 for making the precise position adjustments.

Adjusting the XY-positioning of the sample 102 (i.e. on a plane substantially perpendicular to a light beam emitted from a Raman testing light source 114) may be important for performing Raman scanning on the desired portion of the sample 102, or for testing multiple portions or locations on a sample. However, adjusting a focus of the laser 106 in relation to the sample 102, or a distance (i.e. depth) of the sample 102 in relation to the laser emitter 114, can have drastic effects on the accuracy and precision of the Raman testing. The focus or distance may be referred to as "focus depth," "Z focus," "Z depth," or "Z distance" herein, where Z generally refers to a distance between the laser emitter 114 and the sample 102, or a focal depth of the laser 106.

As stated herein, Z focus refers to the depth focus of the laser 106 on the sample 102. Z focus may be adjusted by physically altering the distance between the laser emitter 114 and the sample 102, such as by moving the laser emitter 114 or the platform 104 on which the sample 102 rests. The platform 104 or adjustable arm 108 may also be capable of making precise tilt angle adjustments to the sample, or the laser emitter 114 may be tilted relative to the sample, to compensate for Z focus length change caused by variations in the tilt or angle of the sample 102 at different locations. In some embodiments, Z focus may be adjusted by modifying the focus of the laser emitter 114 itself, such as by adjusting a focusing lens 116 of the laser emitter 114.

FIG. 2 depicts a table 200 of results of Raman testing under different conditions, including the systems and methods for accurate and precise Raman testing disclosed herein. Specifically, table 200 shows the testing conditions of testing the same sample 102 with and without adjusting the focus of the laser 106. The table 200 includes results both with and without filters applied to reduce non-Raman scattering particles (such as Rayleigh scattering particles). Table 200 demonstrates that accurately adjusting Z focus results in gage sigma at least 45% lower than when Z focus is not adjusted. Thus, adjusting Z focus can result in greatly improved accuracy and precision of the Raman testing process.

Figure 3:
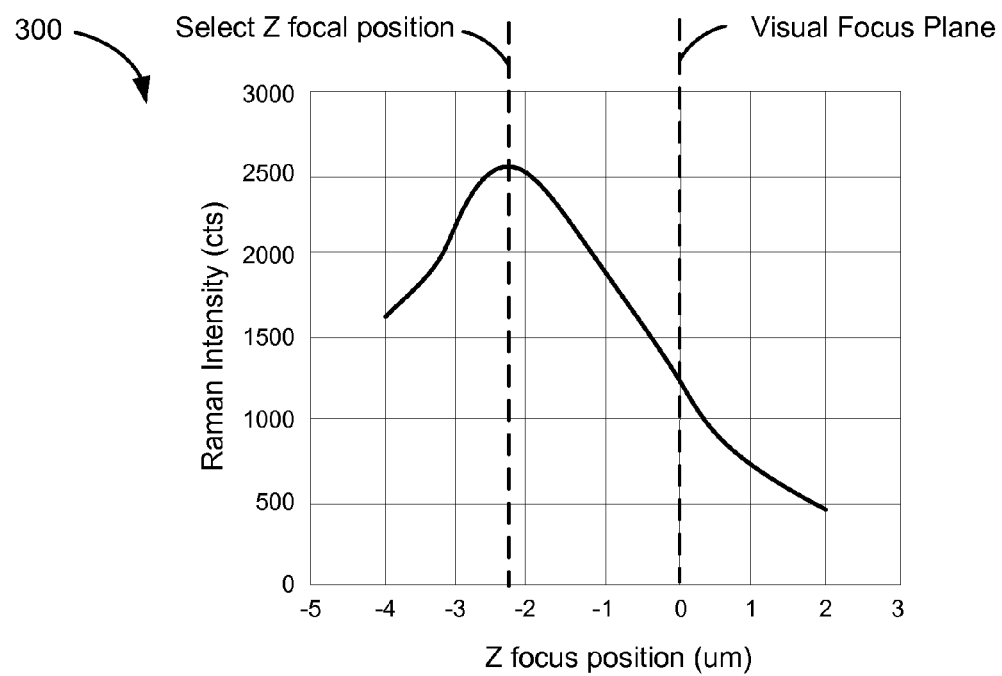
FIG. 3 is a chart of results from another illustrative embodiment of a system for improved accuracy and precision in Raman spectroscopy.

FIG. 3 depicts a chart 300 demonstrating the effect of Z focus on Raman spectra intensity in an example sample test with a system for improved accuracy and precision in Raman spectroscopy. Chart 300 indicates that, while adjusting the Z focus from −4 um to 2 um, the Raman spectra intensity shows a strong dependence on Z focus position. At approximately 2 um below the visual focal plane (e.g. Z=0 um) in the example embodiment, the strongest Raman spectra is obtained. The Z focus with the strongest Raman spectra may provide improved accuracy and precision in results with Raman spectroscopy. In some embodiments, other Z-focuses may be desired, such as just outside peak Raman intensity, or a Z-focus with low Raman intensity.

In addition to the Z-focus, proper XY positioning of a sample can be important. As discussed herein, XY positioning may refer to positioning of a sample on the plane substantially perpendicular to a light beam emitted from a Raman spectra apparatus. It may be beneficial to test the same one or more locations between different or batch-processed samples, which requires precise XY plane adjustment of the laser or of the sample for every test. XY plane adjustment may involve adjusting the sample's relative position, adjusting the samples rotational alignment on the XY plane, or a combination thereof. For example, in a manufacturing context, testing the same locations on each sample can give a better idea of how changes to a manufacturing process impact exact aspects of the produced product, such as a coating thickness in specific locations of the product.

Manually adjusting the positioning of samples can be difficult and time-consuming, especially when dealing with nano-to micro-scale samples. A high-precision piezo scanner (e.g. capable of making adjustments in a nanometer scale) can make minute adjustments in X, Y, and Z coordinates, but may require guidance or instructions on what adjustments to make. This need can be addressed by integrating optical components and computer vision and pattern-recognition software (element 120 of FIG. 1, which may be referred to as "machine vision") with the Raman testing system and piezo scanner combination.

By providing the Raman testing system a "template" image (element 118 of FIG. 1), depicting how a sample should appear relative to the laser testing apparatus, the piezo scanner can be programmed to move the current sample until it comes approximately in line with the template image. The necessary accuracy of matching the current sample to the template image may depend on the sample or the test.

Figure 4:
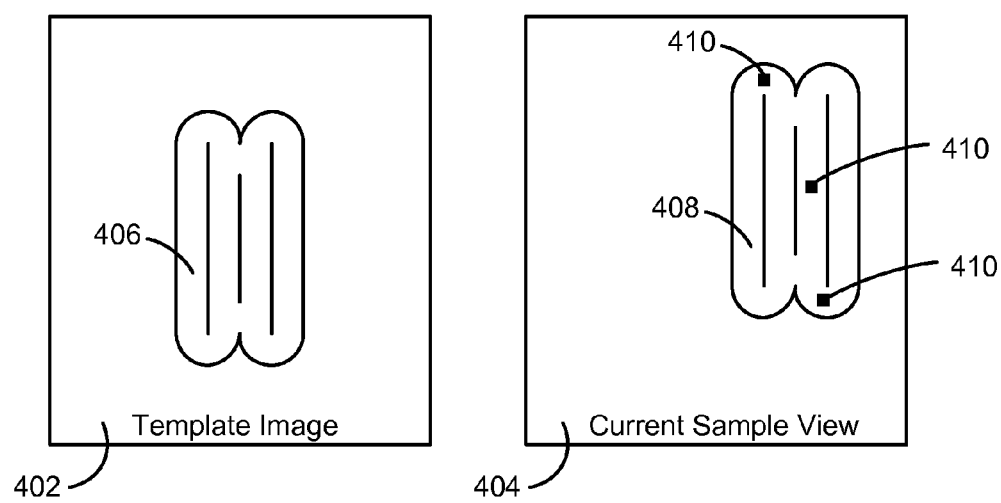
FIG. 4 is a diagram of an illustrative embodiment of a system for improved accuracy and precision in Raman spectroscopy.

FIG. 4 is a diagram of an illustrative embodiment of a system for improved accuracy and precision in Raman spectroscopy using machine vision. A template image 402 can be provided to the Raman system, illustrating a view of a template sample 406 and how it may be centered relative to the testing apparatus. The Raman system may then compare the template image 402 to the current sample view 404, which may be observed through an integrated camera or other optical sensor (element 122 of FIG. 1). The Raman system can then analyze the current sample view 404 image and calculate positional adjustments to bring the current sample 408 approximately in line with the template image 402. In the depicted example, the Raman system would need to move the current sample 408 down and to the left so that it is centered relative to the view 404, as depicted in the template image 402.

Image recognition systems, including the optical sensors 122 for observing images and the software, firmware, configured circuits (e.g. circuit 124 of FIG. 1), etc. for processing images and performing actions based upon them, may be used to allow the Raman system to make the positional adjustments. The image recognition systems can be integrated into the Raman testing/piezo scanner combination, or may be part of external computers and devices configured to function with the Raman system.

The Raman system may also be configured or programmed to test a sample in multiple locations, as depicted by testing locations 410. The template image 402 may identify the testing locations 410, or the Raman system may be configured to test relative XY coordinates once a sample has been properly positioned. In such an embodiment, the Raman testing laser 106 or the scanner platform 104 may need to reposition to test the designated location(s).

Figure 5:
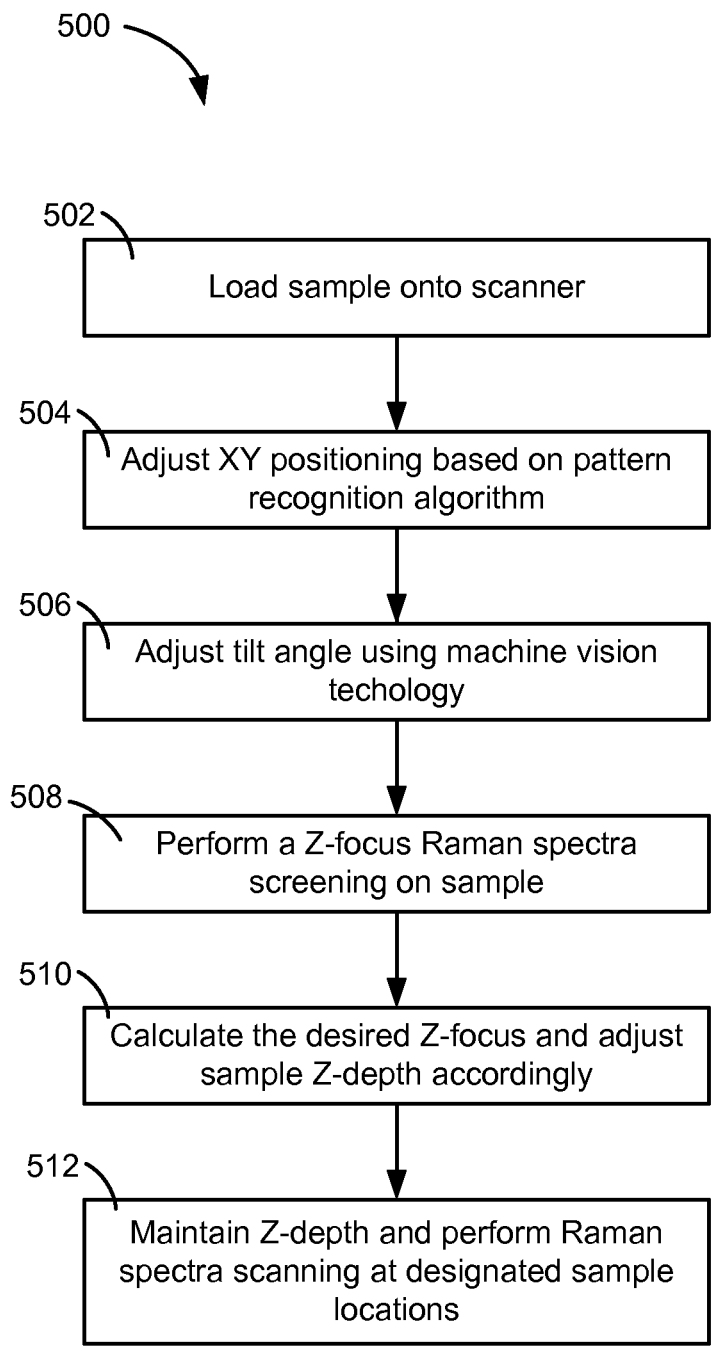
FIG. 5 is a flowchart of another illustrative embodiment of a method for a system for improved accuracy and precision in Raman spectroscopy.

Turning now to FIG. 5, a flowchart of an illustrative embodiment of a method for using a system for improved accuracy and precision in Raman spectroscopy is shown and generally designated 500. The method 500 may involve loading a sample to be tested onto a scanner, at 502. In some embodiments this may involve loading the sample onto an adjustable platform capable of XYZ movement, such as platform 104 in FIG. 1. In other embodiments, the sample platform may be stationary and the Raman testing mechanisms, such as the laser emitter 114 of FIG. 1, may be adjustable relative to the sample, or both the testing mechanisms and the sample may be adjustable.

The method 500 may involve adjusting the XY position of the sample or testing mechanisms, including rotational adjustment on the XY plane, based on a pattern recognition algorithm, at 504. The adjustments to XY position may involve using machine vision technology to compare a template image of a sample to the current sample, and adjust the sample platform or testing apparatus to achieve the desired XY positioning. In some embodiments, manual or semi-manual (e.g. an operator controlling a computer or mechanism) XY positioning may be used in place of or in addition to an automated pattern recognition algorithm.

The method 500 may involve adjusting the tilt angle of the sample or testing mechanisms, at 506. This tilt adjustment may be done manually or semi-manually, may be assisted or implemented using machine vision, or may be done automatically or semi-automatically using pattern recognition algorithms. In some embodiments, adjusting the XY positioning at 504 and adjusting the tilt angle at 506 may be performed concurrently.

A Z focus Raman spectra screening may then be performed on the sample, at 508. A focus screening may involve testing a sample at a range of different Z-foci or Z-depths and monitoring the intensity of the Raman scattering at these focuses or depths. The screening may involve testing a range by selecting a Z-focus or Z-depth, running a Raman test, adjusting the Z-focus or Z-depth, running another Raman test, etc. until the desired range of Z-focuses or Z-depths has been tested. In some embodiments, the Z-focus or Z-depth may be adjusted while the Raman test is in progress.

The Z-focus with the desired intensity Raman spectra (e.g. the maximum intensity Raman spectra) may then be calculated from the screening results, and the corresponding Z-focus may then be set for continued testing, at 510. Additional testing at the selected Z-focus may be performed, or the Raman scattering results observed from the Z-focus spectra screening may be sufficient. For example, the results from the desired intensity Z-focus obtained during the screening may be used as the results of the test.

If additional testing is to be performed, a previously determined Z-focus may be maintained, and Raman spectra scanning may be performed at additional designated sample locations, at 512. Depending on the type of desired results, the shape or nature of the sample, or other considerations, a Z-focus Raman spectra screening 508 may be performed at each designated sample testing location. For example, a sample with a non-uniform depth may benefit from repeated Z-focus screenings at each testing location.

In accordance with various embodiments, the methods described herein may be implemented as one or more software programs running on a computer processor or controller. For example, the methods described herein may be implemented as one or more software programs running on a computing device. Dedicated hardware implementations including, but not limited to, application specific integrated circuits, programmable logic arrays, and other hardware devices can likewise be constructed to implement the methods described herein. Further, the methods described herein may be implemented as a computer readable medium including instructions that when executed cause a processor to perform the methods.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Moreover, although specific embodiments have been illustrated and described herein, it should be appreciated that any subsequent arrangement designed to achieve the same or similar purpose may be substituted for the specific embodiments shown.

This disclosure is intended to cover any and all subsequent adaptations or variations of various embodiments. Combinations of the above embodiments, and other embodiments not specifically described herein, will be apparent to those of skill in the art upon reviewing the description. Additionally, the illustrations are merely representational and may not be drawn to scale. Certain proportions within the illustrations may be exaggerated, while other proportions may be reduced. Accordingly, the disclosure and the figures are to be regarded as illustrative and not restrictive.

What is claimed is:

1. A method comprising:
    adjusting a first position of a sample on a plane substantially perpendicular to an angle of a light beam emitted from a Raman spectroscopic laser;
    adjusting a tilt angle of the sample relative to the Raman spectroscopic laser based on a comparison of an optical image of the sample and a template image;
    performing a first Raman spectra focus screening on the sample to determine a first depth focus setting of the Raman spectroscopic laser in relation to the sample based on a Raman spectra scattering intensity from the first Raman spectra focus screening, a Raman spectra focus screening including measuring the Raman spectra scattering intensity at a range of different depth focus settings of the light beam emitted from the Raman spectroscopic laser; and
    performing a first Raman spectra test on the sample at the first depth focus setting.

2. The method of claim 1, further comprising manually providing input directing a piezo scanner to adjust the first position of the sample.

3. The method of claim 1, further comprising adjusting the first position of the sample based on a pattern-recognition algorithm.

4. The method of claim 3, further comprising the pattern recognition algorithm comparing the template image to a current view of the sample and calculating a position modification necessary to move the sample to match the template image.

5. The method of claim 3 further comprising:
    comparing, via an optical sensor and the pattern-recognition algorithm of a Raman spectroscopic apparatus including the Raman spectroscopic laser, the optical image of the test sample and the template sample image; and
    calculating, via the Raman spectroscopic apparatus, positional adjustments to align the test sample with the template image based on the comparison.

6. The method of claim 1, further comprising:
    adjusting a second position of the sample on the plane substantially perpendicular to the angle of the light beam emitted from the Raman spectroscopic laser; and
    performing a second Raman spectra test on the sample at the second position.

7. The method of claim 6, further comprising:
    performing a second Raman spectra focus screening on the sample at the second position to determine a second depth focus setting of the Raman spectroscopic laser in relation to the sample based on the Raman spectra scattering intensity from the second Raman spectra focus screening; and performing the second Raman spectra test on the sample at the second position using the second depth focus setting.

8. The method of claim 1, further comprising modifying a manufacturing process of the sample based on the results of the first Raman spectra test.

9. The method of claim 1 further comprising:
determining the first depth focus setting from the range of different depth focus settings at which to perform the first Raman spectra test on the sample using the Raman spectroscopic laser, the first depth focus setting determined based on a low measured intensity value of the Raman spectra scattering at the first depth focus setting compared to measured intensities at other depth focus settings from the range of different depth focus settings.

10. The method of claim 1 further comprising:
selecting the first depth focus setting based on a maximum-intensity Raman measured at the range of different depth focus settings.

11. A method comprising:
performing a depth focus Raman spectra screening on a test sample to determine a depth focus for a laser emitter of a Raman spectroscopic apparatus which produces a maximum-intensity Raman spectra, wherein the depth focus spectra screening comprises:
adjusting a tilt angle of the test sample relative to the laser emitter based on a comparison of an optical image of the test sample and a template sample image;
adjusting the laser emitter's depth focus setting separate from a visual focal plane of the Raman spectroscopic apparatus including the laser emitter, the depth focus setting adjusted using a focusing lens of the laser emitter;
performing Raman spectra scans on the test sample at a plurality of depth foci for the laser emitter; and
modifying a process based on a result of the Raman spectra scan at the depth focus with the maximum-intensity Raman spectra.

12. The method of claim 11, further comprising using a piezo scanner to adjust a position of the test sample relative to the laser emitter of the Raman spectroscopic apparatus on a plane substantially perpendicular to an angle of a light beam emitted by the laser emitter of the Raman spectroscopic apparatus.

13. The method of claim 11 further comprising:
manually providing input directing the piezo scanner to adjust the position of the test sample.

14. The method of claim 11 further comprising:
determining a selected depth focus from the plurality of depth foci at which to perform a Raman spectroscopy test on the test sample using the Raman spectroscopic device, the selected depth focus determined based on a low measured intensity value of Raman scattering at the selected depth focus compared to measured intensities at other depth focus settings from the plurality of depth foci.

15. The method of claim 11 further comprising:
modifying the process includes modifying a manufacturing process of samples.

16. The method of claim 11 further comprising:
comparing, via an optical sensor and a pattern-recognition algorithm of the Raman spectroscopic apparatus, the optical image of the test sample and the template sample image; and
calculating, via the Raman spectroscopic apparatus, positional adjustments to align the test sample with the template image based on the comparison.

17. The method of claim 11 further comprising:
adjusting a first position of the test sample on a plane substantially perpendicular to an angle of a light beam emitted from the laser emitter; and
performing the Raman spectra scans on the test sample at the first position.

18. The method of claim 17 further comprising:
adjusting a second position of the test sample on the plane substantially perpendicular to the angle of the light beam emitted from the laser emitter; and
performing Raman spectra scans on the test sample at the second position to determine a second depth focus with the maximum-intensity Raman spectra.

19. The method of claim 18 further comprising:
performing a first Raman spectra test at the first position at the depth focus with the maximum-intensity Raman spectra;
performing a second Raman spectra test on the test sample at the second position using the second depth focus setting; and
modifying the process based on the first Raman spectra test and the second Raman spectra test.

* * * * *